United States Patent
Xu et al.

(10) Patent No.: US 11,327,042 B2
(45) Date of Patent: May 10, 2022

(54) COMPOSITIONS AND METHODS FOR IMPROVED CREATININE MEASUREMENT ACCURACY AND USES THEREOF

(71) Applicant: Instrumentation Laboratory Company, Bedford, MA (US)

(72) Inventors: Xiaoxian Xu, Maynard, MA (US); Prasad Pamidi, Burlington, MA (US); David Raimondi, Bedford, MA (US); Ruchika Malhotra, Arlington, MA (US); Matthew Curley, Acton, MA (US)

(73) Assignee: INSTRUMENTATION LABORATORY COMPANY, Bedford, MA (US)

( * ) Notice: Subject to any disclaimer, the term of this patent is extended or adjusted under 35 U.S.C. 154(b) by 321 days.

(21) Appl. No.: 16/429,993

(22) Filed: Jun. 3, 2019

(65) Prior Publication Data
US 2020/0319211 A1    Oct. 8, 2020

Related U.S. Application Data (60) Provisional application No. 62/830,191, filed on Apr. 5, 2019.

(51) Int. Cl.
| | | |
|---|---|---|
| *G01N 33/70* | (2006.01) | |
| *G01N 33/96* | (2006.01) | |
| *G01N 27/327* | (2006.01) | |
| *C12Q 1/00* | (2006.01) | |
| *G01N 27/333* | (2006.01) | |
| *G01N 27/30* | (2006.01) | |
| *C12Q 1/54* | (2006.01) | |
| *G01N 33/53* | (2006.01) | |
| *G16H 10/40* | (2018.01) | |
| *G16B 25/30* | (2019.01) | |
| *G06F 17/18* | (2006.01) | |
| *C12Q 1/58* | (2006.01) | |
| *G01N 33/543* | (2006.01) | |
| *G06F 30/331* | (2020.01) | |

(52) U.S. Cl.
CPC ......... *G01N 27/3275* (2013.01); *C12Q 1/002* (2013.01); *C12Q 1/003* (2013.01); *C12Q 1/005* (2013.01); *C12Q 1/54* (2013.01); *G01N 27/308* (2013.01); *G01N 27/3272* (2013.01); *G01N 27/3276* (2013.01); *G01N 27/3335* (2013.01); *G01N 33/5308* (2013.01); *G01N 33/70* (2013.01); *G01N 33/96* (2013.01); *G06F 17/18* (2013.01); *G16B 25/30* (2019.02); *G16H 10/40* (2018.01); *C12Q 1/58* (2013.01); *G01N 27/3274* (2013.01); *G01N 33/5438* (2013.01); *G06F 30/331* (2020.01)

(58) Field of Classification Search
CPC .......... C12Q 1/00; C12Q 1/002; C12Q 1/003; C12Q 1/005; G01N 27/308; G01N 27/3271; G01N 27/3272; G01N 27/3274; G01N 27/3275; G01N 27/3276; G01N 27/333; G01N 27/3335; G01N 33/5308; G01N 33/5438; G01N 33/70; G01N 33/96; Y10T 436/147777; Y10T 436/17
USPC ..................... 436/63, 96, 98, 106, 149, 150; 422/82.01, 82.02
See application file for complete search history.

(56) References Cited

U.S. PATENT DOCUMENTS

| | | | |
|---|---|---|---|
| 6,960,466 B2 | 11/2005 | Pamidi et al. | |
| 7,632,672 B2 | 12/2009 | Pamidi et al. | |
| 7,815,788 B2 | 10/2010 | Schaffar et al. | |
| 8,426,192 B2 | 4/2013 | Pamidi et al. | |
| 9,487,811 B2 | 11/2016 | Zhao et al. | |
| 2003/0062262 A1* | 4/2003 | Mansouri ............. | A61B 5/1477 204/400 |
| 2004/0211666 A1 | 10/2004 | Pamidi et al. | |
| 2004/0256227 A1 | 12/2004 | Shin et al. | |
| 2006/0275857 A1 | 12/2006 | Kjaer et al. | |
| 2008/0173064 A1 | 7/2008 | Schaffar et al. | |
| 2012/0181189 A1 | 7/2012 | Merchant | |
| 2017/0254771 A1 | 9/2017 | Balasubramanian et al. | |
| 2017/0260560 A1* | 9/2017 | Merchant ............... | C12Q 1/001 |
| 2017/0363567 A1* | 12/2017 | Kjaer .................... | G01N 33/70 |
| 2017/0363568 A1* | 12/2017 | Hansen ................. | C12Q 1/002 |
| 2020/0319211 A1 | 9/2020 | Xu et al. | |
| 2020/0319210 A1 | 10/2020 | Xu et al. | |

FOREIGN PATENT DOCUMENTS

| | | |
|---|---|---|
| EP | 1753872 B1 | 1/2014 |
| JP | 2004-506224 A | 2/2004 |
| JP | 2007-512519 A | 5/2007 |
| JP | S58-061459 B2 | 11/2015 |
| JP | 2018-500547 A | 1/2018 |
| JP | 2018-500564 A | 1/2018 |

(Continued)

OTHER PUBLICATIONS

International Search Report and Written Opinion for International Application No. PCT/US2019/035152, dated Nov. 8, 2019, 12 pages.
International Search Report and Written Opinion for International Application No. PCT/US2019/035155, dated Nov. 14, 2019, 12 pages.
International Search Report and Written Opinion for International Application No. PCT/US2019/035156, dated Sep. 20, 2019, 12 pages.
Nichols et al., The effect of nitric oxide surface flux on the foreign body response to subcutaneous implants, Biomaterials, vol. 33, No. 27, May 20, 2012, pp. 6305-6312.

(Continued)

*Primary Examiner* — Maureen Wallenhorst
(74) *Attorney, Agent, or Firm* — Burns & Levinson LLP.

(57) ABSTRACT

The disclosure relates to electrochemical sensors for measuring creatinine and creatine in a patient's blood. More particularly, the disclosure relates to compositions and methods for improving measurement accuracy of electrochemical sensors used for measuring creatinine and creatine.

22 Claims, 2 Drawing Sheets

(56) References Cited

FOREIGN PATENT DOCUMENTS

| JP | S64-075000 | B1 | 10/2018 |
|---|---|---|---|
| WO | 98/21356 | A1 | 5/1998 |
| WO | 03/019171 | A1 | 3/2003 |
| WO | 2005/052596 | A1 | 6/2005 |
| WO | 2008/028011 | A2 | 3/2008 |
| WO | 2009/053370 | A1 | 4/2009 |
| WO | 2009/082699 | A1 | 7/2009 |
| WO | 2016/096725 | A1 | 6/2016 |
| WO | 2020204974 | A1 | 10/2020 |

OTHER PUBLICATIONS

Conway et al., Layer-by-layer design and optimization of xerogel-based amperometric first generation biosensors for uric acid, Journal of Electroanalytical Chemistry, vol. 775, May 25, 2016, pp. 135-145.

Tjell et al., Diffusion rate of hydrogen peroxide through water-swelled polyurethane membranes, Sensing and Bio-Sensing Research, vol. 21, No. 27, Nov. 1, 2018, pp. 35-39.

Hydrourethane AdvanSource Biomaterials, Advancesource Biomaterials, Jun. 21, 2011 [retrieved on Sep. 19, 2019]. Retrieved from the Internet URL: http://www.advbiomaterials.com/pdf/HydroThane%20Factsheet.pdf.

Hydromed D Series, Advancesource Biomaterials, Apr. 16, 2010 [retrieved on Sep. 20, 2019]. Retrieved from the Internet URL: http://www.advbiomaterials.com/products/hydrophilic/HydroMed.pdf.

International Search Report and Written Opinion for International Application No. PCT/US2019/035157, dated Dec. 12, 2019, 18 pages.

International Search Report and Written Opinion for International Application No. PCT/US2019/035153, dated Nov. 26, 2019, 12 pages.

International Preliminary Report on Patentability dated Sep. 28, 2021, International Application No. PCT/US2019/035155 filed June 3, 2019 (7 pages).

Examiner Requisition for Canadian Patent Application No. 3,105,011, dated Nov. 19, 2021, 4 pages.

Notice of Reasons for Rejection for Japanese Patent Application No. 2020-570732, dated Jan. 5, 2022, (with English translation), 4 pages.

Notice of Reasons for Rejection for Japanese Patent Application No. 2020-570732, dated Sep. 7, 2021, (with English translation), 8 pages.

\* cited by examiner

COMPOSITIONS AND METHODS FOR IMPROVED CREATININE MEASUREMENT ACCURACY AND USES THEREOF

CROSS-REFERENCE TO RELATED APPLICATIONS

This application claims the benefit of priority of U.S. Provisional Application No. 62/830,191, filed on Apr. 5, 2019, the entire contents of which are hereby incorporated by reference in their entirety.

FIELD OF THE DISCLOSURE

The disclosure relates to electrochemical sensors for measuring creatinine and creatine in a patient's blood. More particularly, the disclosure relates to compositions and methods for improving measurement accuracy of electrochemical sensors used for measuring creatinine and creatine.

BACKGROUND OF THE DISCLOSURE

The ability to accurately measure creatinine and creatine levels in a patient's blood is important. In particular, serum creatinine is an important indicator of renal health because it is excreted unaltered by the kidneys, and can readily be measured. For example, elevated levels of blood serum creatinine is a late marker of chronic kidney disease, and is generally only observed when significant kidney damage has already occurred. Chronic kidney disease refers to the gradual loss of kidney function. The kidneys function to filter wastes and excess fluids from the blood, and these filtered wastes and excess fluids are then excreted in urine. When chronic kidney disease reaches an advanced stage (e.g., end-stage renal disease), dangerous levels of fluids, metabolites, electrolytes, wastes, and the like, can build up in the body. In the early stages of chronic kidney disease, there may be few signs or symptoms, and progression of the disease may not become apparent until kidney function has been significantly impaired.

Creatinine/creatine in a sample (e.g., a patient's blood) may be measured via electrochemical sensors. For example, current creatinine sensors may include an enzymatic biosensor containing three enzymes—creatininase, creatinase, and sarcosine oxidase—that catalyze the production of glycine, formaldehyde, and hydrogen peroxide from creatinine and water. These three enzymes may be immobilized on the surface of a platinum electrode, and the final reaction product of hydrogen peroxide ($H_2O_2$) may then be electrochemically oxidized on the platinum electrode under a constant polarization potential and used to measure creatinine and/or creatine levels in a patient's blood. However, in order to determine creatinine and/or creatine concentrations in a biological sample, the creatinine and creatine sensors need to be calibrated to determine their sensitivities. This can be done by measuring the current responses of creatinine and creatine sensors in calibration solutions with pre-determined concentrations of creatinine and creatine. Once the sensitivities of the creatinine and creatine sensors are determined, the concentrations of creatinine and creatine in any biological sample can be estimated by measuring the current signals of that sample and comparing the measured sensitivities of the creatinine and creatine sensors as determined from the calibration process. Unfortunately, it is non-trivial to accurately measure creatinine levels in biological samples for a variety of reasons. For example, sensor to sensor manufacturing variations that occur during biosensor fabrication/manufacturing may cause variability in creatinine measurement accuracy to occur on a sensor by sensor or sensor apparatus by sensor apparatus basis. Additionally, biological sample matrix variations can also create a major challenge with respect to accurately measuring creatinine levels. Accordingly, there is an urgent unmet need to identify and develop new methodologies to improve biosensor calibration accuracy for creatinine and/or creatine measurement.

SUMMARY OF THE DISCLOSURE

The present disclosure provides compositions and methods for improving the accuracy of creatinine and creatine in biosensors.

In one aspect, the present disclosure provides a method of improving the accuracy of a creatinine/creatine measuring system having a calibrated creatine sensor and a calibrated creatinine sensor, including the steps of: measuring, with the calibrated creatine sensor, a measured creatine sensor current signal (M$\Delta$I2) of a first biological matrix correction solution (BMCS2) having a known concentration of creatine (CR_BMCS2) and a known concentration of creatinine (CREA_BMCS2); determining a measured concentration of creatine (MCR_BMCS2) in BMCS2; comparing MCR_BMCS2 to CR_BMCS2 to determine a creatine sensor biological matrix correction factor ($\Delta$CR); measuring, with the calibrated creatinine sensor, a measured creatinine sensor current signal (M$\Delta$I2') of BMCS2; determining a measured concentration of creatinine (MCREA_BMCS2) in BMCS2; and comparing MCREA_BMCS2 to CREA_BMCS2 to determine a creatinine sensor biological matrix correction factor ($\Delta$CREA).

In an embodiment, CR_BMCS2 and CREA_BMCS2 have stable values.

In an embodiment, the stable values are based on a stable ratio of creatine to creatinine in BMCS2.

In an embodiment, the stable values are based on a storage temperature of BMCS2.

In an embodiment, BMCS2 includes one or more biological matrix factors selected from the group consisting of $Ca^{++}$, $HCO_3^-$, pH, $pCO_2$, $pO_2$, electrolytes, and metabolite.

In an embodiment, $\Delta$CR is applied to a creatine measurement obtained from a biological matrix sample.

In an embodiment, $\Delta$CREA is applied to a creatinine measurement obtained from a biological matrix sample.

In an embodiment, the method further includes the steps of: measuring, with the calibrated creatine sensor, a second measured creatine sensor current signal (M2$\Delta$I2) of a second biological matrix correction solution (BMCS3) having a known concentration of creatine (CR_BMCS3) and a known concentration of creatinine (CREA_BMCS3); determining a measured concentration of creatine (M2CR_BMCS3) in BMCS3; comparing M2CR_BMCS3 to CR_BMCS3 to determine a second creatine sensor biological matrix correction factor ($\Delta$CR'); measuring, with the calibrated creatinine sensor, a measured creatinine sensor current signal (M2$\Delta$I2') of BMCS3; determining a measured concentration of creatinine (M2CREA_BMCS3) in BMCS3; and comparing M2CREA_BMCS3 to CREA_BMCS3 to determine a creatinine sensor biological matrix correction factor ($\Delta$CREA').

In an embodiment, CR_BMCS3 and CREA_BMCS3 have stable values.

In an embodiment, the stable values are based on a stable ratio of creatine to creatinine in BMCS3.

In an embodiment, the stable values are based on a storage temperature of BMCS3.

In an embodiment, BMCS3 includes one or more biological matrix factors selected from the group consisting of $Ca^{++}$, $HCO_{3-}$, pH, $pCO_2$, $pO_2$, electrolytes, and metabolite.

In an embodiment, ΔCR' is applied to a Slope of a creatine measurement obtained from a biological matrix sample.

In an embodiment, ΔCR, ΔCR', ΔCREA, and ΔCREA' are applied to a Slope 1 and a Slope 2 of a creatinine measurement obtained from a biological matrix sample.

In an embodiment, the stable ratio of creatine to creatinine is about 1.5 to about 2.

In an embodiment, the stable ratio of creatine to creatinine is 1.5 to 2.

In an embodiment, BMCS2 or BMCS3, respectively, includes about 2-5 mg/dL of creatine and about 1-3 mg/dL of creatinine.

In an embodiment, the stable values are stable for a minimum of 8 months.

In an embodiment, a concentration of $Ca^{++}$ is between about 0.4 and about 1.6 mg/dL and a concentration of $HCO_{3-}$ is between about 10 and about 30 mg/dL.

In one aspect, the present disclosure provides a creatinine/creatine measuring system that includes: a calibrated creatine sensor; a calibrated creatinine sensor; one or more network interfaces to communicate in a computer network; a processor coupled to the network interfaces and the creatine sensor and the creatinine sensor and adapted to execute one or more processes; and a memory configured to store a process executable by the processor, the process when executed operable to: measure, with the calibrated creatine sensor, a measured creatine sensor current signal (MΔI2) of a first biological matrix correction solution (BMCS2) having a known concentration of creatine (CR_BMCS2) and a known concentration of creatinine (CREA_BMCS2); determine a measured concentration of creatine (MCR_BMCS2) in BMCS2; compare MCR_BMCS2 to CR_BMCS2 to determine a creatine sensor biological matrix correction factor (ΔCR); measure, with the calibrated creatinine sensor, a measured creatinine sensor current signal (MΔI2') of BMCS2; determine a measured concentration of creatinine (MCREA_BMCS2) in BMCS2; and compare MCREA_BMCS2 to CREA_BMCS2 to determine a creatinine sensor biological matrix correction factor (ΔCREA).

By "control" or "reference" is meant a standard of comparison. In one aspect, as used herein, "changed as compared to a control" sample or subject is understood as having a level that is statistically different than a sample from a normal, untreated, or control sample. Control samples include, for example, creatine solutions, creatinine solutions, and the like. Methods to select and test control samples are within the ability of those in the art. Determination of statistical significance is within the ability of those skilled in the art, e.g., the number of standard deviations from the mean that constitute a positive result.

As used herein, "creatine (a.k.a., 2-[Carbamimidoyl (methyl)amino]acetic acid, N-Carbamimidoyl-N-methylglycine, or Methyiguanidoacetic acid)" refers to an organic compound that produce energy for the cells through the recycling of adenosine triphosphate (ATP) by converting adenosine diphosphate (ADP) back to ATP by donating phosphate groups. Creatine has the following chemical structure:

2-[Carbamimidoyl(methyl)amino]acetic acid

As used herein, "creatinine" refers to the enzymatic breakdown by-product of creatine, and is generally found in two major tautomeric forms, which are shown below.

Ranges can be expressed herein as from "about" one particular value, and/or to "about" another particular value. When such a range is expressed, another aspect includes from the one particular value and/or to the other particular value. Similarly, when values are expressed as approximations, by use of the antecedent "about," it is understood that the particular value forms another aspect. It is further understood that the endpoints of each of the ranges are significant both in relation to the other endpoint, and independently of the other endpoint. It is also understood that there are a number of values disclosed herein, and that each value is also herein disclosed as "about" that particular value in addition to the value itself. It is also understood that throughout the application, data are provided in a number of different formats and that this data represent endpoints and starting points and ranges for any combination of the data points. For example, if a particular data point "10" and a particular data point "15" are disclosed, it is understood that greater than, greater than or equal to, less than, less than or equal to, and equal to 10 and 15 are considered disclosed as well as between 10 and 15. It is also understood that each unit between two particular units are also disclosed. For example, if 10 and 15 are disclosed, then 11, 12, 13, and 14 are also disclosed, Ranges provided herein are understood to be shorthand for all of the values within the range. For example, a range of 1 to 50 is understood to include any number, combination of numbers, or sub-range from the group consisting 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 as well as all intervening decimal values between the aforementioned integers such as, for example, 1.1, 1.2, 1.3, 1.4, 1.5, 1.6, 1.7, 1.8, and 1.9. With respect to sub-ranges, "nested sub-ranges" that extend from either end point of the range are specifically contemplated. For example, a nested sub-range of an exemplary range of 1 to 50 may comprise 1 to 10, 1 to 20, 1 to 30, and 1 to 40 in one direction, or 50 to 40, 50 to 30, 50 to 20, and 50 to 10 in the other direction.

Other features and advantages of the disclosure will be apparent from the following description of the preferred embodiments thereof, and from the claims. Unless otherwise defined, all technical and scientific terms used herein have the same meaning as commonly understood by one of ordinary skill in the art to which this disclosure belongs. Although methods and materials similar or equivalent to those described herein can be used in the practice or testing of the present disclosure, suitable methods and materials are described below. All published foreign patents and patent applications cited herein are incorporated herein by reference. All other published references, documents, manuscripts and scientific literature cited herein are incorporated herein by reference. In addition, the materials, methods, and examples are illustrative only and not intended to be limiting.

Where applicable or not specifically disclaimed, any one of the embodiments described herein are contemplated to be able to combine with any other one or more embodiments, even though the embodiments are described under different aspects of the disclosure.

These and other embodiments are disclosed and/or encompassed by, the following Detailed Description.

BRIEF DESCRIPTION OF THE DRAWINGS

The following detailed description, given by way of example, but not intended to limit the disclosure solely to the specific embodiments described, may best be understood in conjunction with the accompanying drawings, in which:

FIGS. 1A-1B show two graphs that that depict the bias of creatinine measured by whole blood creatinine biosensor vs. plasma creatinine on a chemistry analyzer.

DETAILED DESCRIPTION OF THE DISCLOSURE

The present disclosure is based, at least in part, on the discovery that one or more biological matrix correction solutions may be used to create creatine sensor biological matrix correction factors and creatinine sensor biological matrix correction factors. The present disclosure provides that such creatine sensor biological matrix correction factors and creatinine sensor biological matrix correction factors may be applied to measured creatine and/or creatinine values in biological matrix samples to correct for measurement inaccuracies that result from, for example, sensor to sensor manufacturing variations, and the activity of inhibitory factors present in biological matrix samples such as, for example, $HCO_3^-$, $Ca^{++}$, pH, and the like.

Overview

Current creatinine sensors in a creatine/creatinine system (e.g., GEM PAK cartridge) include an enzymatic biosensor containing three enzymes. These enzymes are immobilized on the surface of a platinum electrode. The creatinine detection system is based on the following three enzyme cascade reaction (Rx):

(Rx. 1) creatinine + $H_2O$ ⇌ (creatininase) creatine (Rx. 2) creatine + $H_2O$ → (creatinase) sarcosine + urea (Rx. 3) sarcosine + $H_2O$ + $O_2$ → (sarcosine oxidase) glycine + formaldehyde + $H_2O_2$ The product hydrogen peroxide ($H_2O_2$) is then electrochemically oxidized on the platinum electrode under the constant polarization potential, and the current signal is proportional to the analyte concentration.

The presence of creatine in clinical samples necessitates an additional sensor for creatine measurement to correct for the creatine response of the creatinine sensor. The creatine sensor includes only reactions (2) and (3) of the above enzyme cascade reactions.

Both the creatine and creatinine sensors have a diffusion control membrane (also referred to as an outer membrane) on top of the enzyme layers. The diffusion control membrane limits the flux of creatinine and creatine substrates entering the enzyme layer to ensure that the signals generated by the hydrogen peroxide are proportional to the substrate concentrations of the sample.

In order to determine the respective concentrations of creatinine and creatine in a biological sample(s), the creatinine and creatine sensors need to be calibrated in order to determine their respective sensitivities. This may be achieved by comparing the current signals of the creatinine and creatine sensors in calibration solutions containing pre-determined (e.g., known) concentrations of creatinine and creatine. Once the sensitivities of the creatinine and creatine sensors are determined, the concentrations of creatine and creatinine in any biological sample can be estimated by adjusting the measured readings with the results determined from the calibration process.

For example, calibration systems for a creatine sensor or biosensor may involve a 2-point calibration based on the following equation:

$$\Delta I2 = [CR\_CS2]*Slope \quad (Eq. 1)$$

$\Delta I2$ is a current signal measured on the creatine sensor in a first calibration solution (CS2). [CR_CS2] is the concentration of creatine in the first calibration solution (CS2). As discussed in detail below, CS2 may have a known concentration of creatine (CR_CS2), a known concentration of creatinine (CREA_CS2), and a stable ratio of creatine to creatinine, which makes it possible to establish a creatine sensor sensitivity (Slope) for the creatine sensor.

A calibration system for a creatinine sensor or biosensor may implement a 3-point calibration methodology. As the creatinine sensor provides readings of both creatinine and creatine in biological samples or calibration solutions containing both analytes, the sensitivities of the creatinine sensor to creatinine (Slope1) or creatine (Slope2) may be determined according to the disclosure, as defined below, from equations 2-5 below. The disclosure provides that two calibration solutions with distinct ratios of creatine/creatinine may be used for the 3-point calibration method.

3-point creatinine sensor calibration equations:

$$\Delta I2' = [CREA\_CS2]*Slope1 + [CR\_CS2]*Slope2 \quad (Eq. 2)$$

$$\Delta I3' = [CREA\_CS3]*Slope1 + [CR\_CS3]*Slope2 \quad (Eq. 3)$$

$\Delta I2'$ and $\Delta I3'$ are current signals measured on creatinine sensor in a first calibration solutions (CS2) and a second calibration solution (CS3), respectively. CS3 may have an initial known creatine concentration (CR_CS3), an initial known creatinine concentration (CREA_CS3) and an unstable ratio of creatine to creatinine.

[CREA_CS2], [CREA_CS3], [CR_CS2] and [CR_CS3] represent the initial known concentrations of creatinine and creatine in calibration solutions CS2 and CS3, respectively. The sensitivity of the creatinine sensor for creatinine and creatine, Slope1 (sensor sensitivity to creatinine) and Slope2 (sensor sensitivity to creatine), can be derived from Eq. 2 and 3:

$$\text{Slope1} = ([CR\_CS3]*\Delta I2' - [CR\_CS2]*\Delta I3')/([\text{Creat}\_CS2]*[CR\_CS3] - [\text{Creat}\_CS3]*[CR\_CS2]) \text{ pA/mg/dL} \quad (\text{Eq. 4})$$

$$\text{Slope2} = ([CREA\_CS2]*\Delta I3' - [CREA\_CS3]*\Delta I2')/([\text{Creat}\_CS2]*[CR\_CS3] - [\text{Creat}\_CS3]*[CR\_CS2]) \text{ pA/mg/dL} \quad (\text{Eq. 5})$$

CS2 may be formulated at the optimal stable ratio of creatine/creatinine between about 1.5 and 2, while CS3 may be formulated at a different, unstable, ratio (about 10 to 70) of creatine/creatinine that will vary over time from the original ratio at the time of manufacturing due to concentration changes during storage.

Once properly calibrated, a creatinine measurement system as described above may quantitatively measure the concentration of creatinine in biological samples. However, there are several practical issues associated with sensor variations that result from typical manufacturing processes, calibration and other analyzer operation specific variations, and biological sample matrix variations that present significant challenges with respect to measuring creatinine accurately.

For example, the activity of many enzymes may be inhibited or impacted by specific chemicals (e.g., ions or gases). For example, the above-described three-enzyme system for converting creatinine to $H_2O_2$ is susceptible (e.g., due to inhibition or interference) to many common analytes that may be present in clinical chemistry assays such as, e.g., $HCO_{3-}$ and $Ca^{++}$. Additionally, the three-enzyme system for converting creatinine to $H_2O_2$ is also sensitive to sample pH. Due to differences in the concentration of such analytes in biological samples across different patient samples or populations, it is possible for errors to be introduced when measuring creatinine and/or creatine concentrations in biological samples. Prior art solutions to address these problems have included the application of sensor measurement algorithms to account for such effects. As an added complication, sensor measuring systems are prone to manufacturing deviations that may produce sensor to sensor variability during the manufacturing process. For example, normal variations in sensor outer membrane composition or enzyme membrane thickness may produce significant errors that result from the enzyme inhibitory effects due to relative diffusion of analyte(s) versus an inhibitory chemical(s). Unfortunately, the enzyme inhibitory effects that may be found within biological samples and produce measurement errors may be additive in their effect when present in combination with typical sensor to sensor manufacturing variations; consequently, the combination of variable enzyme inhibitory effects within biological sample matrices and sensor to sensor manufacturing variability may act in concert (e.g., synergistically) to generate larger measurement error deviations.

Calibration Matrix

It is common among clinical chemistry analyzers to offer multiple analyte assays for a single sample measurement. In order to provide results for multiple analytes in a single measurement, up to three biological matrix correction solutions with varying levels of analytes may be used for calibration and estimation of sensor sensitivity. For example, for calibrating the pH and levels of $pCO_2$, $pO_2$, electrolytes or metabolites, two calibration reagent solutions with significantly different levels of each of the analytes may be used. However, for calibrating the creatinine sensor, three calibration reagent solutions with significantly varying levels of analytes may be used. The calibration reagent solutions used for calibrating a creatinine sensor according to the disclosure comprise one or more analytes in addition to creatinine, and may be used for calibrating other types of sensors. Some of the one or more analytes present in these calibration reagent solutions may have an inhibitory effect on the ability of the creatinine sensor to measure creatinine. For example, pH, $HCO_{3-}$, and $Ca^{++}$ levels in these reagents will affect creatinine or creatine sensor calibrations and may also have the potential to produce sensor specific errors in calibration. The errors could be attributed to subtle variations from sensor to sensor and the inhibitory effects arising from the above-described specific analytes.

Biological Sample Matrix

Creatinine concentrations in biological samples may typically be very low (e.g., about 0.04 to about 1.10 mg/dL) compared to glucose concentrations (e.g., about 65 to about 95 mg/dL) or the concentration of analytes that have inhibitory effects (e.g., $Ca^{++}$: about 4 to about 6 mg/dL or $HCO_{3-}$: about 19 to about 26 mmol/L) on the sensors. Low concentrations of creatinine in biological samples, loss of creatinine due to the presence of diffusion controlled outer membranes, and the three enzyme conversion process of the sensor all act in combination to produce very low electrical signals. Conversely, the presence of relatively high concentrations of analytes that could produce inhibitory effects on creatinine measurement may have a significant impact at such low electrical signals.

One prior art solution to this problem is to use calibration solutions. For example, in this approach the first step is to create correction factors for each individual analyte with variable levels of creatinine, creatine, and inhibitors or interfering compounds present in the calibration solutions. Disadvantageously, this approach requires many assumptions to be made before a simple correction factor can be derived. Additionally, the impact of simultaneous interactions of multiple inhibitors or interfering compounds on enzyme activities is also not taken into consideration. As a result, the effectiveness of this prior art approach is questionable due to the assumptions that are required. Unfortunately, there are currently no good prior art solutions available to address the practical issue of measuring creatinine levels in biological samples that may display significant sample to sample biological matrix variations.

The present disclosure provides compositions and methods for correcting errors that may arise throughout the diagnostic cycle from sensor calibration to biological sample matrix measurement. Importantly, the techniques herein provide biological matrix correction solutions that are designed to be matched (or paired) with common biological samples that contain inhibitory analytes known to impact the activities of the creatinine/creatine three enzyme system. These solutions may have pre-determined creatinine and creatine concentrations that are stable due to stable creatine/creatinine ratios or optimized storage conditions in combination with clinical reference ranges of analytes that have an inhibitory or interfering effect on the enzymes used in creatinine sensors (e.g., creatininase, creatinase, sarcosine oxidase, and the like). Once a creatinine and/or creatine sensor has been installed and calibrated, the correction solutions disclosed herein may be measured on the creatinine and/or creatine sensors and the responses measured for the calibration reagents and the correction solutions for both creatinine and creatine are obtained and analyzed to identify sensor specific correction factors. These correction factors may be determined for all subsequent biological samples throughout the lifetime usage of the sensor without repeating this process at each instance of sensor calibration.

The techniques herein provide a creatinine measuring system that may include three major steps: sensor calibration, establishing correction factors, and sample measurements as described in detail below.

Sensor Calibration

Creatinine measuring systems contains both creatinine and creatine sensors. The sensors are subjected to calibration solutions with pre-determined creatinine and creatine concentrations periodically throughout the sensor lifetime usage. Once determined, these sensitivities may be used for subsequent sample measurements. In the multi-analyte clinical chemistry analyzer (e.g., GEM PAK cartridge), the calibration reagent solutions may also contain $HCO_{3-}$, $Ca^{++}$, and pH, which are known to impact the creatinine or creatine enzyme sensors. As these solutions all serve as shared calibration solutions for multiple analytes such as, for example, $HCO_{3-}$, $Ca^{++}$ and pH, they cannot all be formulated so as to match exactly the biological sample matrix. Therefore, the sensor sensitivities that are obtained from the calibration process are not identical to the sensitivities measured in the biological sample matrix. Additionally, such deviations are not consistent from sensor to sensor due to the subtle variations that may occur during the manufacturing process for multilayer sensor structures.

Creatinine/Creatine Correction Solutions

The techniques herein provide one or more specific creatinine/creatine solutions to simulate the biological sample matrix with analytes known to inhibit or interfere with creatinine or creatine enzyme sensors.

A first correction solution may have pre-determined creatinine and creatine concentrations in the matrix with inhibitory/interfering factors such as, for example, $HCO_{3-}$ (e.g., at about 20 mM), $Ca^{++}$ (e.g., at about 0.8 mM), pH (e.g., at about 7.4), and $pCO_2$ (e.g., at about 30 mmHg), or within the range of $HCO_{3-}$ (e.g., about 10 to about 30 mM), $Ca^{++}$ (e.g., about 0.4 to about 1.6 mM), pH (e.g., about 7.0 to 8.0), and $pCO_2$ (e.g., about 15 to about 45 mmHg), which are concentrations that are all close to a normal clinical sample matrix.

A second correction solution may also be provided that is similar to the biological matrix, but with different levels of creatinine and creatine.

These correction solutions may be stored in either sealed reagent bags or in ampules to maintain the constant $pCO_2$ and pH levels. These solutions may be buffered, supplemented with biocides, and maintained at optimal storage temperatures to ensure reagent stability. These correction solutions may be measured as samples during sensor installation and completion of the initial calibration process.

Establishing the Individual Sensor Correction Factors for Creatinine and Creatine The creatinine/creatine correction solution may be measured on each creatinine or creatine measuring system during sensor installation and after initial calibration to establish the sensor sensitivities. Measured creatinine and creatine concentrations from the sensors are compared to the pre-determined creatinine and creatine levels of the correction solutions to establish the correction factors for both creatinine and creatine sensors respectively.

Alternatively, two correction solutions can be measured consecutively after sensor installation, which can provide more accurate correction factors as a result of measuring the two distinct levels of creatinine and creatine.

These correction factors provide the sensitivity deviation in biological matrix versus the sensitivities obtained in calibration solutions for the specific creatinine and creatine sensors.

According to the techniques herein, the accuracy of a creatinine/creatine measuring system having a calibrated creatine sensor and a calibrated creatinine sensor may be improved by measuring, with the calibrated creatine sensor, a measured creatine sensor current signal (M$\Delta$I2) of a first biological matrix correction solution (BMCS2) having a known concentration of creatine (CR_BMCS2) and a known concentration of creatinine (CREA_BMCS2); determining a measured concentration of creatine (MCR_BMCS2) in BMCS2; comparing MCR_BMCS2 to CR_BMCS2 to determine a creatine sensor biological matrix correction factor ($\Delta$CR); measuring, with the calibrated creatinine sensor, a measured creatinine sensor current signal (M$\Delta$I2') of BMCS2; determining a measured concentration of creatinine (MCREA_BMCS2) in BMCS2; and comparing MCREA_BMCS2 to CREA_BMCS2 to determine a creatinine sensor biological matrix correction factor ($\Delta$CREA).

To provide a biological matrix correction value/factor, CR_BMCS2 and CREA_BMCS2 may have stable values. For example, such stable values may be based on a stable ratio of creatine to creatinine in BMCS2, or on a storage temperature of BMCS2.

According to the techniques herein, biological matrix correction solutions disclosed herein may include, but are not limited to, one or more biological matrix factors selected from the group consisting of $Ca^{++}$, $HCO_{3-}$, pH, $pCO_2$, $pO_2$, other electrolytes, and metabolites.

Once obtained, $\Delta$CR may be applied to a creatine measurement obtained from a biological matrix sample, while $\Delta$CREA may be applied to a creatinine measurement obtained from a biological matrix sample.

According to the techniques herein, the accuracy of a creatinine/creatine measuring system having a calibrated creatine sensor and a calibrated creatinine sensor may be further improved by including the additional steps of: measuring, with the calibrated creatine sensor, a second measured creatine sensor current signal (M2$\Delta$I2) of a second biological matrix correction solution (BMCS3) having a known concentration of creatine (CR_BMCS3) and a known concentration of creatinine (CREA_BMCS3); determining a measured concentration of creatine (M2CR_BMCS3) in BMCS3; comparing M2CR_BMCS3 to CR_BMCS3 to determine a second creatine sensor biological matrix correction factor ($\Delta$CR'); measuring, with the calibrated creatinine sensor, a measured creatinine sensor current signal (M2$\Delta$I2') of BMCS3; determining a measured concentration of creatinine (M2CREA_BMCS3) in BMCS3; and comparing M2CREA_BMCS3 to CREA_BMCS3 to determine a creatinine sensor biological matrix correction factor ($\Delta$CREA').

As discussed above for the first biological matrix correction solution, CR_BMCS3 and CREA_BMCS3 may have stable values that may be based on a stable ratio of creatine to creatinine in BMCS3 or a storage temperature of BMCS3 (e.g., 4° C.).

Once obtained, $\Delta$CR' may be applied to a Slope of a creatine measurement obtained from a biological matrix sample, while $\Delta$CR, $\Delta$CR', $\Delta$CREA and $\Delta$CREA' may be applied to a Slope 1 and a Slope 2 of a creatinine measurement obtained from a biological matrix sample.

In embodiments of the disclosure, the stable ratio of creatine to creatinine is about 1.5 to about 2, or is 1.5 to 2.

In embodiments of the disclosure, BMCS2 or BMCS3, respectively, may include about 2-5 mg/dL of creatine and about 1-3 mg/dL of creatinine.

According to the techniques herein, the stable values of the above-described biological matrix correction solutions may be stable for a minimum of 8 months.

In embodiments of the disclosure, a concentration of $Ca^{++}$ is between about 0.4 and about 1.6 mmol/L and a concentration of $HCO_{3-}$ is between about 10 and about 30 mmol/L.

Measuring Creatinine/Creatine in Biological Samples

For each patient sample, the current signals are measured on creatinine and creatine sensors, and then the sensitivities from the most recent calibration are used to estimate the creatinine and creatine concentrations in the patient sample. The correction factors may then be applied to the measured concentrations to produce final creatinine and creatine measurement results.

Alternatively, the corrections can be applied to the original sensitivities obtained from the calibration process. In this approach, the correction factors obtained from the correction solutions are directly applied to the sensitivities from the most recent sensor calibration. Then the sample creatinine and creatine concentrations are estimated from sample current signals and the corrected sensitivities.

Kits

The instant disclosure also provides kits containing agents of this disclosure for use in the methods of the present disclosure. Kits of the instant disclosure may include one or more containers comprising an agent (e.g., creatine, creatinine, etc.) of this disclosure and/or may contain agents in one or more correction solutions containing analytes such as, for example, $HCO_{3-}$, and $Ca^{++}$. Additionally, kits of the present disclosure may also include correction solutions that are adjusted to a variety of different pH levels. In some embodiments, the kits further include instructions for use in accordance with the methods of this disclosure. In some embodiments, these instructions comprise a description of how to apply the agents/solutions to a sensor (e.g., a creatine sensor, creatinine sensor, and the like) and how to calculate variables of interest (e.g., biological matrix factors such as $Ca^{++}$ correction factor, $HCO_{3-}$ correction factor, pH correction factor, $pCO_2$ correction factor, $pO_2$ correction factor, electrolyte(s) correction factor, metabolite(s) correction factor, and the like) according to any of the methods of the disclosure. In some embodiments, the instructions comprise a description of how to install and calibrate a measuring system as disclosed herein.

The instructions generally include information as to rea Yea/solution concentration, reagent/solution ratio (e.g., creatine/creatinine ratio), shelf life, etc. Instructions supplied in the kits of the instant disclosure are typically written instructions on a label or package insert (e.g., a paper sheet included in the kit), but machine-readable instructions (e.g., instructions carried on a magnetic or optical storage disk) are also acceptable.

The label or package insert indicates that the reagents/solutions may be used to calibrate any of a variety of creatine and/or creatinine sensor(s) for use in a measuring system as described herein. Instructions may be provided for practicing any of the methods described herein, for example, to install and calibrate a measuring system.

The kits of this disclosure are in suitable packaging. Suitable packaging includes, but is not limited to, vials, ampules, bottles, jars, flexible packaging (e.g., sealed Mylar or plastic bags), and the like. Also contemplated are packages for use in combination with a specific device, such as GEM Premier whole blood analyzer family (Instrumentation Laboratory, Bedford, Mass.), In certain embodiments, at least one active agent in the reagent or solution is creatine and/or creatinine.

Kits may optionally provide additional components such as buffers and interpretive information. Normally, the kit comprises a container and a label or package insert(s) on or associated with the container.

The practice of the present disclosure employs, unless otherwise indicated, conventional techniques of chemistry, molecular biology, microbiology, recombinant DNA, genetics, immunology, cell biology, cell culture and transgenic biology, which are within the skill of the art. See, e.g., Maniatis et al., 1982, Molecular Cloning (Cold Spring Harbor Laboratory Press, Cold Spring Harbor, N.Y.); Sambrook et al., 1989, Molecular Cloning, 2nd Ed. (Cold Spring Harbor Laboratory Press, Cold Spring Harbor, N.Y.); Sambrook and Russell, 2001, Molecular Cloning, 3rd Ed. (Cold Spring Harbor Laboratory Press, Cold Spring Harbor, N.Y.); Ausubel et al., 1992), Current Protocols in Molecular Biology (John Wiley & Sons, including periodic updates); Glover, 1985, DNA Cloning Press, Oxford); Anand, 1992; Guthrie and Fink, 1991; Harlow and Lane, 1988, Antibodies, (Cold Spring Harbor Laboratory Press, Cold Spring Harbor, N.Y.); Jakoby and Pastan, 1979; Nucleic Acid Hybridization (B. D. Hames & S. J. Higgins eds. 1984); Transcription And Translation (B. D. Hames & S. J. Higgins eds. 1984); Culture Of Animal Cells (R. I. Freshney, Alan R. Liss, Inc., 1987); Immobilized Cells And Enzymes (IRL Press, 1986); B. Perbal, A Practical Guide To Molecular Cloning (1984); the treatise, Methods In Enzymology (Academic Press, Inc., N.Y.); Gene Transfer Vectors For Mammalian Cells (J. H. Miller and M. P. Calos eds., 1987, Cold Spring Harbor Laboratory); Methods In Enzymology, Vols. 154 and 155 (Wu et al. eds.), Immunochemical Methods in Cell And Molecular Biology (Mayer and Walker, eds., Academic Press, London, 1987); Handbook Of Experimental Immunology, Volumes I-IV (D. M. Weir and C. C. Blackwell, eds., 1986); Riott, Essential Immunology, 6th Edition, Blackwell Scientific Publications, Oxford, 1988; Hogan et al., Manipulating the Mouse Embryo, (Cold Spring Harbor Laboratory Press, Cold Spring Harbor, N.Y., 1986); Westerfield, M., The zebrafish book. A guide for the laboratory use of zebrafish (Danio rerio), (4th Ed., Univ. of Oregon Press, Eugene, 2000).

Unless otherwise defined, all technical and scientific terms used herein have the same meaning as commonly understood by one of ordinary skill in the art to which this disclosure belongs. Although methods and materials similar or equivalent to those described herein can be used in the practice or testing of the present disclosure, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

The present disclosure also relates to a computer system involved in carrying out the methods of the disclosure relating to both computations and sequencing.

A computer system (or digital device) may be used to receive, transmit, display and/or store results, analyze the results, and/or produce a report of the results and analysis. A computer system may be understood as a logical apparatus that can read instructions from media (e.g. software) and/or network port (e.g. from the internet), which can optionally be connected to a server having fixed media. A computer system may comprise one or more of a CPU, disk drives, input devices such as keyboard and/or mouse, and a display (e.g. a monitor). Data communication, such as transmission of instructions or reports, can be achieved through a communication medium to a server at a local or a remote location. The communication medium can include any means of transmitting and/or receiving data. For example, the communication medium can be a network connection, a wireless connection, or an internet connection. Such a connection can provide for communication over the World Wide Web. It is envisioned that data relating to the present disclosure can be transmitted over such networks or connections (or any other suitable means for transmitting information, including but not limited to mailing a physical report, such as a print-out) for reception and/or for review by a receiver. The receiver can be but is not limited to an individual, or electronic system (e.g. one or more computers, and/or one or more servers). The computer system may be integral to, or separate and apart from, a creatinine/creatine biosensor system/apparatus.

In some embodiments, the computer system may comprise one or more processors. Processors may be associated with one or more controllers, calculation units, and/or other units of a computer system, or implanted in firmware as desired. If implemented in software, the routines may be stored in any computer readable memory such as in RAM, ROM, flash memory, a magnetic disk, a laser disk, or other suitable storage medium. Likewise, this software may be delivered to a computing device via any known delivery method including, for example, over a communication channel such as a telephone line, the internet, a wireless connection, etc., or via a transportable medium, such as a computer readable disk, flash drive, etc. The various steps may be implemented as various blocks, operations, tools, modules and techniques which, in turn, may be implemented in hardware, firmware, software, or any combination of hardware, firmware, and/or software. When implemented in hardware (e.g., a creatinine/creatine biosensor system/apparatus), some or all of the blocks, operations, techniques, etc. may be implemented in, for example, a custom integrated circuit (IC), an application specific integrated circuit (ASIC), a field programmable logic array (FPGA), a programmable logic array (PLA), etc.

A client-server, relational database architecture can be used in embodiments of the disclosure. A client-server architecture is a network architecture in which each computer or process on the network is either a client or a server. Server computers are typically powerful computers dedicated to managing disk drives (file servers), printers (print servers), or network traffic (network servers). Client computers include PCs (personal computers) or workstations on which users run applications, as well as example output devices as disclosed herein. Client computers rely on server computers for resources, such as files, devices, and even processing power. In some embodiments of the disclosure, the server computer handles all of the database functionality. The client computer can have software that handles all the front-end data management and can also receive data input from users.

A machine readable medium which may comprise computer-executable code may take many forms, including but not limited to, a tangible storage medium, a carrier wave medium or physical transmission medium. Non-volatile storage media include, for example, optical or magnetic disks, such as any of the storage devices in any computer(s) or the like, such as may be used to implement the databases, etc. shown in the drawings. Volatile storage media include dynamic memory, such as main memory of such a computer platform. Tangible transmission media include coaxial cables; copper wire and fiber optics, including the wires that comprise a bus within a computer system. Carrier-wave transmission media may take the form of electric or electromagnetic signals, or acoustic or light waves such as those generated during radio frequency (RF) and infrared (IR) data communications. Common forms of computer-readable media therefore include for example: a floppy disk, a flexible disk, hard disk, magnetic tape, any other magnetic medium, a CD-ROM, DVD or DVD-ROM, any other optical medium, punch cards paper tape, any other physical storage medium with patterns of holes, a RAM, a ROM, a PROM and EPROM, a FLASH-EPROM, any other memory chip or cartridge, a carrier wave transporting data or instructions, cables or links transporting such a carrier wave, or any other medium from which a computer may read programming code and/or data. Many of these forms of computer readable media may be involved in carrying one or more sequences of one or more instructions to a processor for execution.

The subject computer-executable code can be executed on any suitable device which may comprise a processor, including a server, a PC, or a mobile device such as a smartphone or tablet. Any controller or computer optionally includes a monitor, which can be a cathode ray tube ("CRT") display, a flat panel display (e.g., active matrix liquid crystal display, liquid crystal display, etc.), or others. Computer circuitry is often placed in a box, which includes numerous integrated circuit chips, such as a microprocessor, memory, interface circuits, and others. The box also optionally includes a hard disk drive, a floppy disk drive, a high capacity removable drive such as a writeable CD-ROM, and other common peripheral elements. Inputting devices such as a keyboard, mouse, or touch-sensitive screen, optionally provide for input from a user. The computer can include appropriate software for receiving user instructions, either in the form of user input into a set of parameter fields, e.g., in a GUI, or in the form of preprogrammed instructions, e.g., preprogrammed for a variety of different specific operations.

Reference will now be made in detail to exemplary embodiments of the disclosure. While the disclosure will be described in conjunction with the exemplary embodiments, it will be understood that it is not intended to limit the disclosure to those embodiments. To the contrary, it is intended to cover alternatives, modifications, and equivalents as may be included within the spirit and scope of the disclosure as defined by the appended claims.

EXAMPLES

The present disclosure is further illustrated by the following examples, which should not be construed as limiting. The contents of all references, and published patents and patent applications cited throughout the application are hereby incorporated by reference. Those skilled in the art will recognize that the disclosure may be practiced with variations on the disclosed structures, materials, compositions and methods, and such variations are regarded as within the scope of the disclosure.

Example 1: Bias Charts of Whole Blood Creatinine Samples Measured by GEM PAK Cartridges Vs. Plasma Creatinine by Chemistry Analyzer with and without Biological Matrix Correction Techniques The bias (the difference of creatinine measured between GEM PAK and a reference chemistry analyzer) of the whole blood clinical samples with two solution matrix correction is minimized to meet the clinical requirements.

Figure 1A:
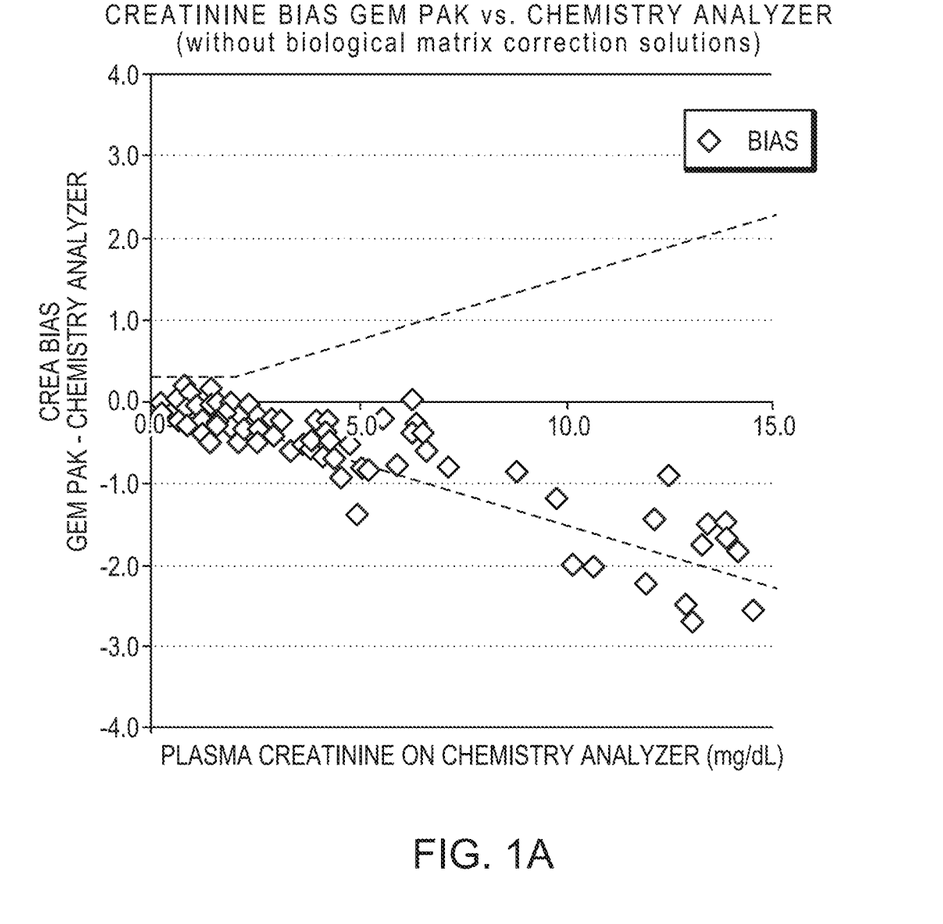
FIG. 1A shows creatinine measurement without correction.
Figure 1B:
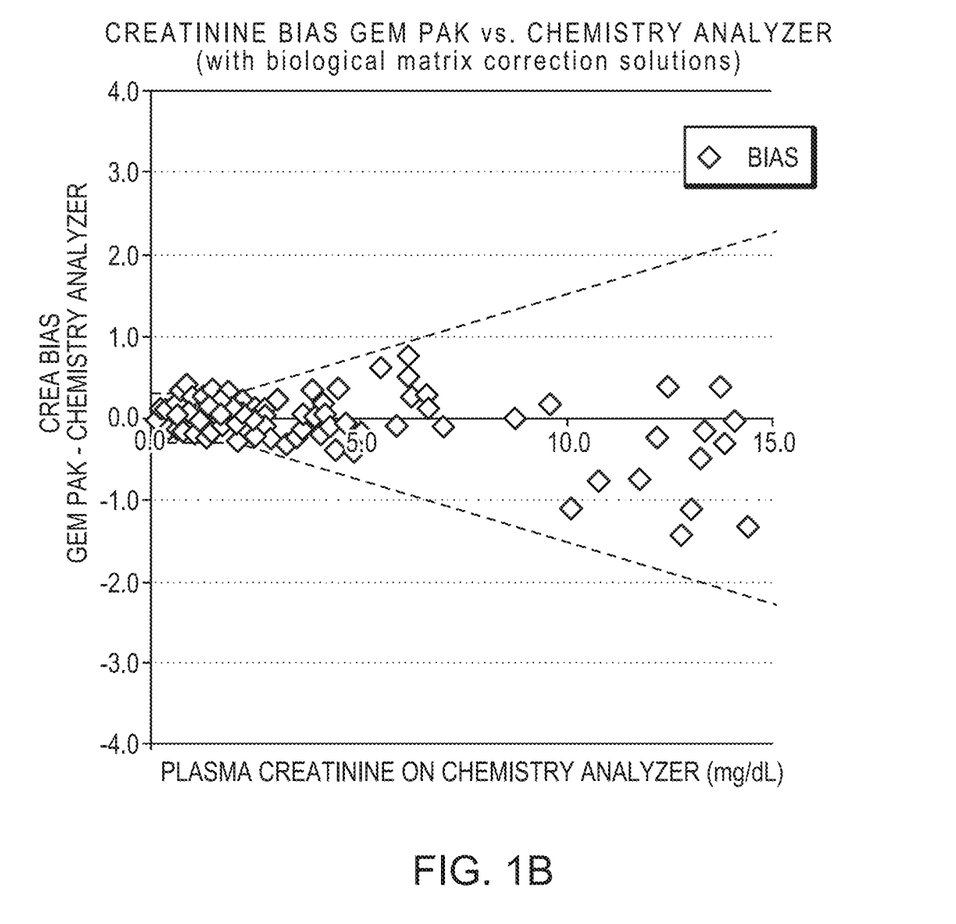
FIG. 1B shows creatinine measurement from the same samples as FIG. 1A, but with creatine and creatinine sensitivity correction with two correction solutions.

In this study each test cartridge contained a creatinine measuring system plus two external correction solutions. The creatinine measuring system comprised of a creatinine sensor, a creatine sensor, three calibration solutions (CS1, CS2, and CS3), and two external biological matrix correction solutions (BMCS2 and BMCS3). Two approaches to establish creatine and creatinine concentrations of whole blood samples were investigated: Option (a) without applying any creatine and creatinine biological matrix corrections for samples measured by the GEM PAK; and Option (b) creatine and creatinine in whole blood clinical samples were corrected based on correction factors established by measuring BMCS2 and BMCS3 in the beginning of each PAK's use life, and followed by applying the correction factors on creatine and creatinine slopes throughout the use life. FIG. 1A indicates that by applying Option (a) to the creatinine and the bias of reported creatinine for all whole blood clinical samples were noticeably negative and somewhat scattered against acceptable clinical specifications (refer to the data points in blue diamond vs. the dotted lines). FIG. 1B demonstrated that by applying Option (b) to the creatinine sample algorithm both the negative bias and scattering of reported creatinine in whole blood clinical samples were significantly reduced throughout the sample range to meet desired clinical specifications (refer to again the data points in blue diamond vs. the dotted lines).

INCORPORATION BY REFERENCE

All documents cited or referenced herein and all documents cited or referenced in the herein cited documents, together with any manufacturer's instructions, descriptions, product specifications, and product sheets for any products mentioned herein or in any document incorporated by reference herein, are hereby incorporated by reference, and may be employed in the practice of the disclosure.

EQUIVALENTS

It is understood that the detailed examples and embodiments described herein are given by way of example for illustrative purposes only, and are in no way considered to be limiting to the disclosure. Various modifications or changes in light thereof will be suggested to persons skilled in the art and are included within the spirit and purview of this application and are considered within the scope of the appended claims. Additional advantageous features and functionalities associated with the systems, methods, and processes of the present disclosure will be apparent from the appended claims. Moreover, those skilled in the art will recognize, or be able to ascertain using no more than routine experimentation, many equivalents to the specific embodiments of the disclosure described herein. Such equivalents are intended to be encompassed by the following claims.

We claim:

1. A method used with a calibrated creatine sensor and a calibrated creatinine sensor, the method comprising:
   (a) measuring, with the calibrated creatine sensor, a measured creatine sensor current signal (M$\Delta$I2) of a first biological matrix correction solution (BMCS2) having a known concentration of creatine (CR_BMCS2), a known concentration of creatinine (CREA_BMCS2), and a predefined concentration of one or more biological matrix factors, where a predefined concentration of a biological matrix factor is an amount within a normal biological sample;
   (b) determining a creatine sensor biological matrix correction factor ($\Delta$CR) based on a measured concentration of creatine (MCR_BMCS2) in BMCS2 and CR_BMCS2, where MCR_BMCS2 is based on M$\Delta$I2;
   (c) measuring, with the calibrated creatinine sensor, a measured creatinine sensor current signal (M$\Delta$I2') of the BMCS2; and
   (d) determining a creatinine sensor biological matrix correction factor ($\Delta$CREA) based on a measured concentration of creatinine (MCREA_BMCS2) in the BMCS2 and CREA_BMCS2, where MCREA_BMCS2 is based on M$\Delta$I2';
   wherein CR_BMCS2 and CREA_BMCS2 have stable values based on a storage temperature of BMCS2 or based on a stable ratio of creatine to creatinine in BMCS2.

2. The method of claim 1, wherein the one or more biological matrix factors in BMCS2 comprise one or more of $Ca^{++}$, $HCO_{3-}$, pH, $pCO_2$ or $pO_2$.

3. The method of claim 2, wherein a concentration of $Ca^{++}$ is between about 0.4 and about 1.6 mg/dL and a concentration of $HCO_{3-}$ is between about 10 and about 30 mmol/L.

4. The method of claim 1, further comprising:
   applying $\Delta$CR to a creatine measurement obtained from a biological matrix sample.

5. The method of claim 1, wherein $\Delta$CREA is applied to a creatinine measurement obtained from a biological matrix sample.

6. The method of claim 1, further comprising:
   (e) measuring, with the calibrated creatine sensor, a second measured creatine sensor current signal (M2$\Delta$I2) of a second biological matrix correction solution (BMCS3) having a known concentration of creatine (CR_BMCS3), a known concentration of creatinine (CREA_BMCS3), and the predefined concentration of one or more biological matrix factors;
   (f) determining a second creatine sensor biological matrix correction factor ($\Delta$CR') based on a measured concentration of creatine (M2CR_BMCS3) in BMCS3 and CR_BMCS3, where M2CR_BMCS3 is based on M2$\Delta$I2;
   (g) measuring, with the calibrated creatinine sensor, a second measured creatinine sensor current signal (M2$\Delta$I2') of the BMCS3; and
   (h) determining a second creatinine sensor biological matrix correction factor ($\Delta$CREA') based on a measured concentration of creatinine (M2CREA_BMCS3) in the BMCS3 and CREA_BMCS3, where M2CREA_BMCS3 is based on M2$\Delta$I2';
   wherein CR_BMCS3 and CREA_BMCS3 have stable values based on a storage temperature of BMCS3 or based on a stable ratio of creatine to creatinine in BMCS3.

7. The method of claim 6, wherein the one or more biological matrix factors in BMCS3 comprise one or more of $Ca^{++}$, $HCO_{3-}$, pH, $pCO_2$ or $pO_2$.

8. The method of claim 6, wherein further comprising:
   applying $\Delta$CR' to a Slope of a creatine measurement obtained from a biological matrix sample.

9. The method of claim 6, wherein $\Delta$CR, $\Delta$CR', $\Delta$CREA and $\Delta$CREA' are applied to a Slope 1 and a Slope 2 of a creatinine measurement obtained from a biological matrix sample.

10. The method of claim 6, wherein BMCS2 or BMCS3, respectively, comprises about 2-5 mg/dL of creatine and about 1-3 mg/dL of creatinine.

11. The method of claim 1, wherein the stable ratio of creatine to creatinine is 1.5 to 2.

12. The method of claim 1, wherein the stable values are stable for a minimum of 8 months.

13. A creatinine/creatine measuring system, comprising:
a calibrated creatine sensor;
a calibrated creatinine sensor;
one or more network interfaces to communicate in a computer network;
a processor coupled to the network interfaces and the creatine sensor and the creatinine sensor and adapted to execute one or more processes; and
a memory storing instructions for a process that is executable by the processor, the process comprising operations to:
(a) measure, with the calibrated creatine sensor, a measured creatine sensor current signal (M$\Delta$I2) of a first biological matrix correction solution (BMCS2) including a known concentration of creatine (CR_BMCS2), a known concentration of creatinine (CREA_BMCS2), and a predefined concentration of one or more biological matrix factors, where a predefined concentration of a biological matrix factor is an amount within a normal biological sample;
(b) determine a creatine sensor biological matrix correction factor ($\Delta$CR) based on a measured concentration of creatine (MCR_BMCS2) in BMCS2 and CR_BMCS2, where MCR_BMCS2 is based on M$\Delta$I2;
(c) measure, with the calibrated creatinine sensor, a measured creatinine sensor current signal (M$\Delta$I2') of BMCS2; and
(d) determine a creatinine sensor biological matrix correction factor ($\Delta$CREA) based on a measured concentration of creatinine (MCREA_BMCS2) in the BMCS2 and CREA_BMCS2, where MCREA_BMCS2 is based on M$\Delta$I2';
wherein CR_BMCS2 and CREA_BMCS2 have stable values based on a storage temperature of BMCS2 or based on a stable ratio of creatine to creatinine in BMCS2.

14. The creatinine/creatine measuring system of claim 13, wherein the process further comprises operations to:
(e) measure, with the calibrated creatine sensor, a second measured creatine sensor current signal (M2$\Delta$I2) of a second biological matrix correction solution (BMCS3) having a known concentration of creatine (CR_BMCS3), a known concentration of creatinine (CREA_BMCS3), and the predefined concentration of one or more biological matrix factors;
(f) determine a second creatine sensor biological matrix correction factor ($\Delta$CR') based on a measured concentration of creatine (M2CR_BMCS3) in BMCS3 and CR_BMCS3, where M2CR_BMCS3 is based on M2$\Delta$I2;
(g) measure, with the calibrated creatinine sensor, a second measured creatinine sensor current signal (M2$\Delta$I2') of the BMCS3; and;
(h) determine a second creatinine sensor biological matrix correction factor ($\Delta$CREA') based on a measured concentration of creatinine (M2CREA_BMCS3) in the BMCS3 and CREA_BMCS3, where M2CREA_BMCS3 is based on M2$\Delta$I2';
wherein CR_BMCS3 and CREA_BMCS3 have stable values based on a storage temperature of BMCS3 or based on a stable ratio of creatine to creatinine in BMCS3.

15. The creatinine/creatine measuring system of claim 14, wherein the operations comprise:
applying $\Delta$CR, $\Delta$CR', $\Delta$CREA and $\Delta$CREA' to a Slope 1 and a Slope 2 of a creatinine measurement obtained from a biological matrix sample.

16. The creatinine/creatine measuring system of claim 14, wherein the stable values are based on a stable ratio of creatine to creatinine in BMCS3.

17. The creatinine/creatine measuring system of claim 14, wherein the one or more biological matrix factors comprise one or more of $Ca^{++}$, $HCO_{3-}$, pH, $pCO_2$, or $pO_2$.

18. The creatinine/creatine measuring system of claim 14, wherein the operations comprise:
applying $\Delta$CR' to a Slope of a creatine measurement obtained from a biological matrix sample.

19. The creatinine/creatine measuring system of claim 13, wherein the one or more biological matrix factors comprise one or more of $Ca^{++}$, $HCO_{3-}$, pH, $pCO_2$, or $pO_2$.

20. The creatinine/creatine measuring system of claim 13, wherein the operations comprise:
applying $\Delta$CR to a creatine measurement obtained from a biological matrix sample.

21. The creatinine/creatine measuring system of claim 13, wherein the operations comprise:
applying $\Delta$CREA to a creatinine measurement obtained from a biological matrix sample.

22. The creatinine/creatine measuring system of claim 13, wherein the stable ratio of creatine to creatinine is 1.5 to 2.

* * * * *